(12) United States Patent
Amin et al.

(10) Patent No.: US 11,185,658 B2
(45) Date of Patent: Nov. 30, 2021

(54) INTERNET OF THINGS (IOT) REAL-TIME RESPONSE TO DEFINED SYMPTOMS

(71) Applicant: International Business Machines Corporation, Armonk, NY (US)

(72) Inventors: Mahmoud Amin, Poughkeepsie, NY (US); Krishna R. Tunga, Wappingers Falls, NY (US); Lawrence A. Clevenger, Saratoga Springs, NY (US); Zhenxing Bi, Niskayuna, NY (US); Leigh Anne H. Clevenger, Rhinebeck, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 171 days.

(21) Appl. No.: 16/217,926

(22) Filed: Dec. 12, 2018

(65) Prior Publication Data

US 2020/0066127 A1   Feb. 27, 2020

Related U.S. Application Data

(63) Continuation-in-part of application No. 16/106,872, filed on Aug. 21, 2018, now abandoned.

(51) Int. Cl.
*A61M 21/02* (2006.01)
*G08B 21/02* (2006.01)
(Continued)

(52) U.S. Cl.
CPC .......... *A61M 21/02* (2013.01); *A61B 5/7264* (2013.01); *A61B 5/7405* (2013.01); *A61B 5/747* (2013.01);
(Continued)

(58) Field of Classification Search
CPC .................. A61M 21/00; A61M 21/02; A61M 2021/0022; A61M 2021/0027;
(Continued)

(56) References Cited

U.S. PATENT DOCUMENTS 6,354,299 B1  3/2002 Fischell et al.
6,759,961 B2  7/2004 Fitzgerald et al.
(Continued)

FOREIGN PATENT DOCUMENTS

GB       2532745 A    6/2016

OTHER PUBLICATIONS aplanforliving.com, "6 Wearables to Track Your Emotions," Retrieved Jun. 13, 2018, 3 pages.
(Continued)

*Primary Examiner* — Carrie R Dorna
(74) *Attorney, Agent, or Firm* — Amin, Turocy & Watson, LLP

(57) ABSTRACT

Systems, computer-implemented methods and/or computer program products that facilitate real-time response to defined symptoms are provided. In one embodiment, a computer-implemented method comprises: monitoring, by a system operatively coupled to a processor, a state of an entity; detecting, by the system, defined symptoms of the entity by analyzing the state of the entity; and transmitting, by the system, a signal that causes audio response or a haptic response to be provided to the entity, wherein transmission of the signal that causes the audio response or the haptic response is based on detection of the defined symptoms.

20 Claims, 10 Drawing Sheets

(51) Int. Cl.
  *A61B 5/00* (2006.01)
  *H04L 29/08* (2006.01)
  *G08B 7/06* (2006.01)
  *A61H 1/00* (2006.01)
(52) U.S. Cl.
  CPC ............ *A61B 5/749* (2013.01); *A61B 5/7455* (2013.01); *A61H 1/00* (2013.01); *G08B 7/06* (2013.01); *G08B 21/02* (2013.01); *H04L 67/12* (2013.01); *A61H 2201/5007* (2013.01); *A61H 2205/062* (2013.01); *A61H 2205/081* (2013.01)
(58) Field of Classification Search
  CPC .. A61M 2021/0061; A61M 2021/0088; G08B 21/0446; G08B 21/0453
  See application file for complete search history.

(56) References Cited

U.S. PATENT DOCUMENTS

| | | | |
|---|---|---|---|
| 2004/0130449 A1 | 7/2004 | Hung | |
| 2008/0171914 A1* | 7/2008 | Ouwerkerk | A61B 5/486 600/300 |
| 2008/0269629 A1* | 10/2008 | Reiner | A61B 5/4836 600/544 |
| 2012/0182143 A1* | 7/2012 | Gaines | A61B 5/0022 340/539.12 |
| 2012/0323090 A1 | 12/2012 | Bechtel et al. | |
| 2016/0022193 A1 | 1/2016 | Rau et al. | |
| 2017/0189639 A1* | 7/2017 | Mastrianni | A61M 21/02 |
| 2017/0238812 A1 | 8/2017 | Atlas | |
| 2017/0258398 A1 | 9/2017 | Jackson | |
| 2017/0261365 A1 | 9/2017 | Kovacs | |
| 2017/0372020 A1 | 12/2017 | Govro et al. | |
| 2018/0104439 A1* | 4/2018 | Tzvieli | A61B 5/015 |

OTHER PUBLICATIONS

Hao, et al., "A visual feedback design based on a brain-computer interface to assist users regulate their emotional state," Apr. 26-May 1, 2014, 2 pages.

Heisig, et al., "Augmented Human: Human OS for Improved Mental Function," Cognitive Computing for Augmented Human Intelligence: Papers from the AAAI-14 Workshop, 2014, 4 pages.

Moraveji, et al., "BreathTray: augmenting respiration self-regulation without cognitive deficit," CHI '12, May 5-10, 2012, 2 pages.

Hao, et al., "cHRV Uncovering Daily Stress Dynamics Using Bio-Signal from Consumer Wearables," MEDINFO 2017, 5 pages.

Blum, et al., "Expressing Human State via Parameterized Haptic Feedback for Mobile Remote Implicit Communication," AH '16 Proceedings of the 7th Augmented Human International Conference 2016, 2 pages.

buy.garmin.com, "fenix 3 HR," retrieved Jun. 13, 2018, 13 pages.

fitbit.com, "Fitbit Retailers," retrieved Jun. 13, 2018, 3 pages.

indigogo.com, "H2: The First Wearable Blood Pressure Monitor," retrieved Jun. 13, 2018, 11 pages.

amazon.com, "UP4 by Jawbone Heart Rate, Activity + Sleep Tracker," retrieved Jun. 13, 2018, 9 pages.

Meuret, et al., "Respiratory Feedback for Treating Panic Disorder," JCLP/In Session, vol. 60(2), 197-207 (2004), 11 pages.

Seliger, "Massage Therapy for Stress Relief and Much More," retrieved Jun. 13, 2018, 6 pages.

mayoclinic.org, "Massage: Get in touch with its many benefits," retrieved Jun. 13, 2018, 4 pages.

Bashivan, et al., "Mental State Recognition via Wearable EEG," Last Accessed: Jun. 18, 2018, 10 pages.

mi.com, "Mi Band," retrieved Jun. 13, 2018, 8 pages.

Mimo, "Sleep trackers for little ones," Last Accessed: Jun. 18, 2018, 7 pages.

korfx.com, "KOR-FX Haptic Gaming Vest Online Store," retrieved Jun. 13, 2018, 3 pages.

Berger, et al., "Stress Reduction and Mood Enhancement in Four Exercise Modes: Swimming, Body Conditioning, Hatha Yoga, and Fencing," 1988. vol. 59. No 2., 13 pages.

indiegogo.com, "Scanadu Scout," retrieved Jun. 13, 2018, 10 pages.

buy.garmin.com, "vivoactive," retrieved Jun. 13, 2018, 9 pages.

apple.com, "Watch—Apple," retrieved Jun. 18, 2018, 9 pages.

Brown, et al., "Sudarshan Kriya Yogic Breathing in the Treatment of Stress, Anxiety, and Depression: Part II—Clinical Applications and Guidelines," vol. 11, No. 4, 2005, pp. 711-717.

Ma, et al., "Health Internet of Things: Recent Applications and Outlook," Journal of Internet Technology vol. 16 (2015) No. 2, 12 pages.

indiegogo.com, "ZENTA: Stress & Emotion Management On Your Wrist," retrieved Jun. 13, 2018, 11 pages.

List of IBM Patents or Applications Treated as Related.

Mel, et al., "The NIST Definition of Cloud Computing," Special Publication 800-145, Sep. 2011, 7 pages.

* cited by examiner

INTERNET OF THINGS (IOT) REAL-TIME RESPONSE TO DEFINED SYMPTOMS

BACKGROUND

The subject disclosure relates to facilitating real-time response to defined symptoms, more specifically, facilitating real-time response to defined symptoms by employing Internet of Things (IoT).

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products that facilitate real-time response to defined symptoms are provided.

According to one embodiment, a system is provided. The system can comprise a memory that stores computer executable components. The system can also comprise a processor, operably coupled to the memory, and that can execute computer executable components stored in the memory. The computer executable components can comprise one or more sensors that monitor a state of an entity. The computer executable components can further comprise a machine learning component that detects defined symptoms of the entity by analyzing the state of the entity. The computer executable components can further comprise a response component that transmits a signal that causes audio response or a haptic response to be provided to the entity, wherein transmission of the signal that causes the audio response or the haptic response is based on detection of the defined symptoms.

According to another embodiment, a computer-implemented method is provided. The computer-implemented method can comprise monitoring, by a system operatively coupled to a processor, a state of an entity. The computer-implemented method can further comprise detecting, by the system, defined symptoms of the entity by analyzing the state of the entity. The computer-implemented method can further comprise transmitting, by the system, a signal that causes audio response or a haptic response to be provided to the entity, wherein transmission of the signal that causes the audio response or the haptic response is based on detection of the defined symptoms.

According to another embodiment, a computer program product is provided. The computer program product can comprise a computer readable storage medium having program instructions embodied therewith. The program instructions can be executable by a processor to cause the processor to monitor a state of an entity. The program instructions can further be executable by the processor to cause the processor to detect defined symptoms of the entity by analyzing the state of the entity. The program instructions can further be executable by the processor to cause the processor to transmit a signal that causes audio response or a haptic response to be provided to the entity, wherein transmission of the signal that causes the audio response or the haptic response is based on detection of the defined symptoms.

DETAILED DESCRIPTION

Figure 1:
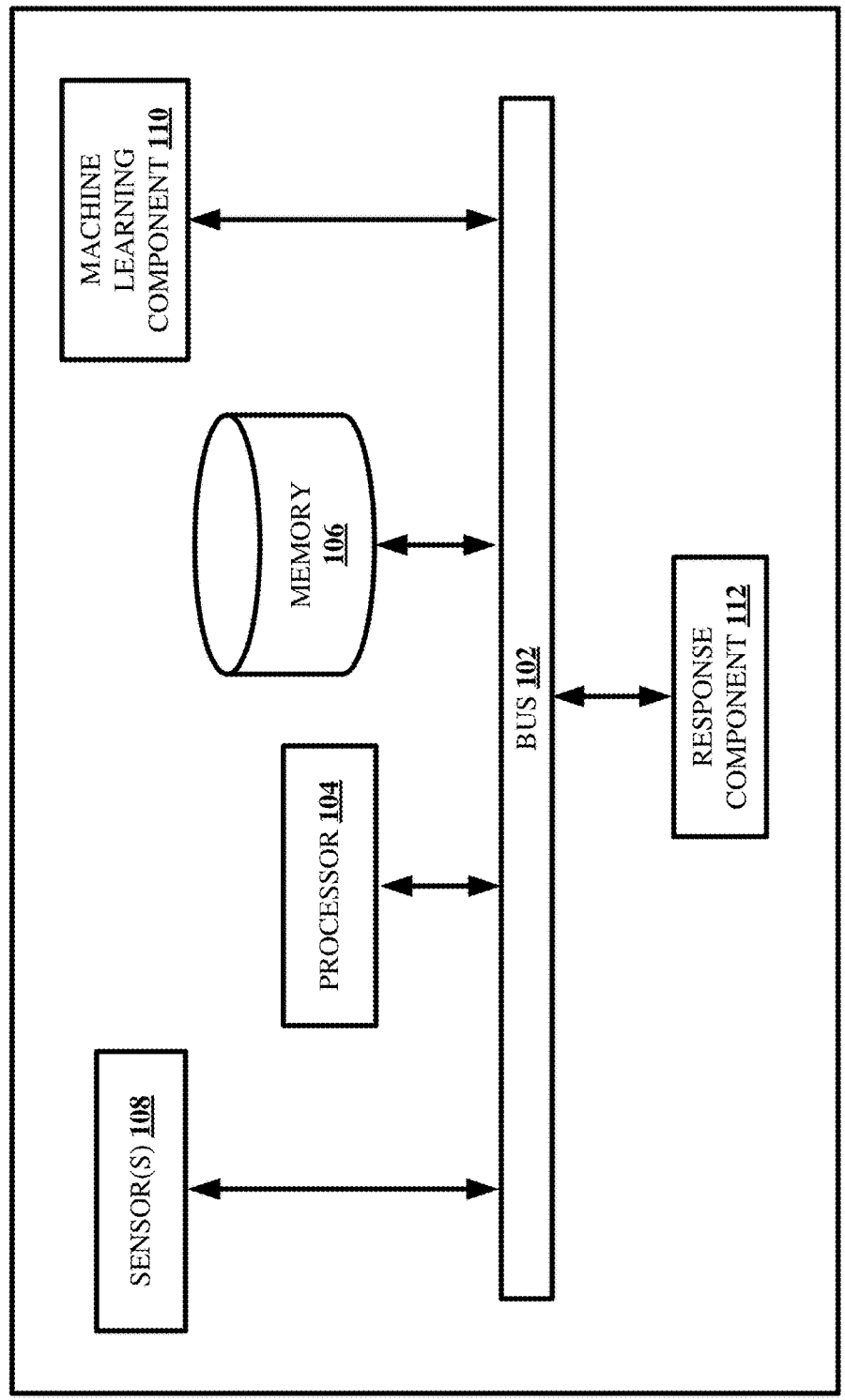
FIG. 1 illustrates a block diagram of an example, non-limiting system facilitating real-time response to defined symptoms in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

One or more embodiments described herein can employ Internet of Things (IoT) to facilitate real-time response to defined symptoms. The embodiments described herein can continually monitor a user (e.g., entity) to detect if the user is exhibiting defined symptoms and quickly attempt to respond in less than a minute. The defined symptoms of a user can be based on changes from baseline in, but not limited to, voice, heart rate, pulse, muscle tension, body movement, body temperature, electrodermal activity, step counts, sleep pattern, geolocation, altitude, atmospheric pressure, light intake, breathing rate, blood pressure, electrical activity of a user's heart, or blood oxygen level. For example, the defined symptoms can be a change or increase or decrease (e.g., out of range) in tone of voice, heart rate, pulse, muscle tension, body movement, body temperature, electrodermal activity, step counts, sleep pattern, geolocation, altitude, atmospheric pressure, light intake, breathing rate, blood pressure, electrical activity of a user's heart, or blood oxygen level. Detection of defined symptoms exhibited by a user can be performed through multiple IoT sensors. Responses can be deployment of soothing actions such as playing breathing exercise, playing relaxing music, playing heartbeat noises, providing haptic shoulder and back massages, etc. The IoT device can also detect if a user is responding to the soothing actions for feedback. If the defined symptoms increase as a function of time, the IoT device can utilize another relaxation method (e.g., soothing action). If attempts to reduce the defined symptoms fail after a determined amount of time, the IoT device can send a notification to alert another person (e.g., a caregiver, a family member, a close friend, etc.) or emergency service for help.

Existing IoT devices such as smartwatches or fitness bands can be utilized or sensors can be embedded in cloths (e.g., smart clothing). Sensors in existing IoT devices or embedded in cloths can detect voice of a user by employing a microphone, detect heart rate of a user by employing a heart rate monitor, detect pulse of a user by employing a pulse monitor, detect muscle tension of a user by employing an electromyography (EMG), measure body movement of a user by employing an accelerometer, measure body temperature of a user by employing a thermometer, measure electrodermal activity of a user by employing a galvanic skin response (GSR), count steps of a user by employing a pedometer, track sleep pattern of a user by employing a sleep monitor, track geolocation of a user by employing a global positioning system (GPS), monitor altitude of a user by employing an altimeter, measure atmospheric pressure surrounding a user by employing a barometer, measure light intake by a user by employing a light sensor, measure breathing rate of a user by employing a respiratory rate monitor, measure blood pressure of a user by employing a blood pressure monitor, monitor electrical activity of a user's heart by employing an electrocardiographic (ECG) sensor, or monitor blood oxygen level of a user by employing a pulse oximeter.

For example, a wearable IoT device can be incorporated into a back brace to address a user's fear of heights. Height fearing users can wear a back brace (e.g., safety equipment to prevent hyperextension of the back) incorporated with an IoT device. Sensors in the IoT device can monitor, but not limited to, a user's voice, body movements and body vitals to detect for defined symptoms. During a vertical rise of an aerial lift, the IoT device can provide gentle vibrating shoulder or back massage to reduce the defined symptoms until the aerial lift unloads the user off the aerial lift. The IoT device can continually monitor the user to make sure the defined symptoms have reduced or subsided.

In another example, a wearable IoT device can address a user's fear of confined spaces such as subways. Sensors in the IoT device can monitor, but not limited to, a user's voice, body movements and body vitals to detect defined symptoms. The IoT device can play breathing exercise recording and/or relaxing music into a user's headphones. The IoT can continually monitor a user to make sure the defined symptoms have reduced or subsided. If the user's defined symptoms is at a critical level (e.g., higher than a determined threshold), the IoT device can call for help.

The subject disclosure is directed to computer processing systems, computer-implemented methods, apparatus and/or computer program products that facilitate efficiently and automatically (e.g., without direct human involvement) real-time response to defined symptoms. Humans are also unable to perform the embodiments described herein as they include, and are not limited to, performing, e.g., complex Markov processes, Bayesian analysis, or other artificial intelligence-based techniques based on probabilistic analyses and evaluating electronic information indicative of real-time response to defined symptoms, and/or determining whether countless multitudes of probability values assigned to real-time response to defined symptoms exceed or fall below various defined probability values.

The computer processing systems, computer-implemented methods, apparatus and/or computer program products employ hardware and/or software to solve problems that are highly technical in nature. For example, problems are related to automated processing, determining or inferring real-time defined symptoms exhibited by a user. These problems are not abstract and cannot be performed as a set of mental acts by a human. For example, a human, or even thousands of humans, cannot efficiently, accurately and effectively manually apply countless or thousands of user data (e.g., audio data, accelerometer data, body vitals, etc.) and perform analysis to provide real-time response to defined symptoms to a user or to notify another person or emergency service for help.

To aid in the numerous inferences described herein (e.g., inferring defined symptoms exhibited by a user, inferring response to defined symptoms, etc.), components described herein can examine the entirety or a subset of data to which it is granted access and can provide for reasoning about or inferring states of a system, environment, etc., from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data.

Such inference can result in construction of new events or actions from a set of observed events and/or stored event data, whether the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

FIG. 1 illustrates a block diagram of an example, non-limiting system 100 facilitating real-time response to defined symptoms in accordance with one or more embodiments described herein. Aspects of systems (e.g., non-limiting system 100 and the like), apparatuses or processes explained in this disclosure can constitute machine-executable components embodied within machines, e.g., embodied in one or more computer readable mediums (or media) associated with one or more machines. Such components, when executed by the one or more machines, e.g., computers, computing devices, virtual machines, etc., can cause the machines to perform the operations described.

In various embodiments, the system 100 can be any type of component, machine, device, facility, apparatus, and/or instrument that comprises a processor. In some embodiments, the system 100 is capable of effective and/or operative communication with a wired and/or wireless network. Components, machines, apparatuses, devices, facilities, and/or instrumentalities that can comprise the system 100 can include, but are not limited to, tablet computing devices, handheld devices, server class computing machines and/or databases, laptop computers, notebook computers, desktop computers, cell phones, smart phones, consumer appliances and/or instrumentation, industrial and/or commercial devices, digital assistants, multimedia Internet enabled phones, multimedia players, and the like.

As illustrated in FIG. 1, the system 100 can comprise a bus 102, processor 104, memory 106, one or more sensors 108 (e.g., sensor 108 or sensors 108), machine learning component 110 and/or response component 112. The bus 102 that can provide for interconnection of various components of the system 100. The processor 104 and memory 106 can carry out computation and/or storage operations of the system 100 as described herein. It is to be appreciated that in some embodiments one or more system components can communicate wirelessly with other components, through a direct wired connection or integrated on a chipset.

In various embodiments, the sensors 108 can continually monitor a state of a user to detect if the user is exhibiting defined symptoms. The system 100 can employ sensors 108 from existing devices (not shown) such as, but not limited to, smartwatches, fitness bands or smart clothing. The sensors 108 can also be embedded in cloth worn by a user. Different types of sensors (e.g. sensors 108) can be employed to monitor the audio of a room or area surrounding a user, detect a user's body vitals or monitor accelerometer data from movements exerted by a user. The sensors 108 can be, but not limited to, a microphone, a heart rate monitor, a pulse monitor, an electromyography (EMG) sensor, an accelerometer, a thermometer, a galvanic skin response (GSR) sensor, a pedometer, a sleep monitor, a global positioning system (GPS), an altimeter, a barometer, a light sensor, a respiratory rate monitor, a blood pressure monitor, an electrocardiographic (ECG) sensor, or a pulse oximeter. It is appreciated that additional sensors not mentioned can be utilized.

A microphone can be employed to detect voice of a user for signs of grunting, screaming, heavy breathing, call for help, etc. A heart rate monitor can be employed to detect heart rate of a user. A pulse monitor can be employed to detect pulse of a user. An electromyography (EMG) sensor can be employed to detect muscle tension of a user. An accelerometer (e.g., 3-axis accelerometer) can be employed to measure body movement of a user such as abnormal or erratic movements of the arms, legs, turning of the body, etc.

A thermometer can be employed to measure body temperature of a user such as increasing or decreasing of body temperature. A galvanic skin response (GSR) sensor can be employed to measure electrodermal activity (e.g., variation in electrical characteristics of the skin) of a user. A pedometer can be employed to count steps of a user. A sleep monitor can be employed to track sleep pattern of a user. A global positioning system (GPS) can be employed to track geolocation of a user. An altimeter can be employed to monitor altitude of a user. A barometer can be employed to measure atmospheric pressure surrounding a user. A light sensor can be employed to measure light intake by a user. A respiratory rate monitor can be employed to measure breathing rate of a user. A blood pressure monitor can be employed to measure blood pressure of a user. An electrocardiographic (ECG) sensor can be employed to monitor electrical activity of a user's heart. A pulse oximeter can be employed to monitor blood oxygen level of a user.

The machine learning component 110 can employ data (e.g., sensor data) detected from the sensors 108. The machine learning component 110 can employ sensor data to detect defined symptoms of a user. The machine learning component 110 can detect defined symptoms by analyzing the state of the user. Based on the detected defined symptoms, the machine learning component 110 can also identify need for help. For example, the machine learning component 110 can utilize voice recognition to detect a call for help from a user. The machine learning component 110 can learn a user's baseline state to detect for changes from the sensors 108. Analyses by the machine learning component 110 can be performed within a device (not shown) worn by a user or through cloud computing.

Based on detection of defined symptoms of a user, responses can be deployed for real-time response to defined symptoms. The responses can comprise, but not limited to, breathing exercise, sound of relaxing music, heartbeat sounds, haptic shoulder or back massage, etc. More specifically, the response component 112 can transmit a signal that can cause audio response or a haptic response to be provided to a user. The transmission of the signal that can cause the audio response or the haptic response can be based on detection of the defined symptoms. For example, upon detection of the defined symptoms by the machine learning component 110, the response component 112 can transmit a signal that can cause the audio response or the haptic response. Audio responses can comprise, but not limited to, breathing exercise, sound of relaxing music, heartbeat sounds, etc. Haptic responses can comprise, but not limited to, haptic shoulder massages, haptic back massages, etc.

The response component 112 can generate the audio response or the haptic response at a time period less than 1 minute from time of detection of the defined symptoms. The response component 112 can change the audio response or the haptic response based on determination that the defined symptoms have increased over time. For example, in some embodiments, the machine learning component 110 can continually analyze sensor data monitored by the sensors 108 to determine whether the defined symptoms have increased or improvements were made. The response component 112 can employ this feedback from the machine learning component 110 to determine which audio response or haptic response should be deployed and transmit a signal that can cause that response. It is appreciated that the response component 112 can transmit more than one signal to cause more than one response to be deployed at a given moment. In a non-limiting example, the response component 112 can transmit a signal to cause relaxing music to be played and haptic back massages to be provided at the same time.

Figure 2:
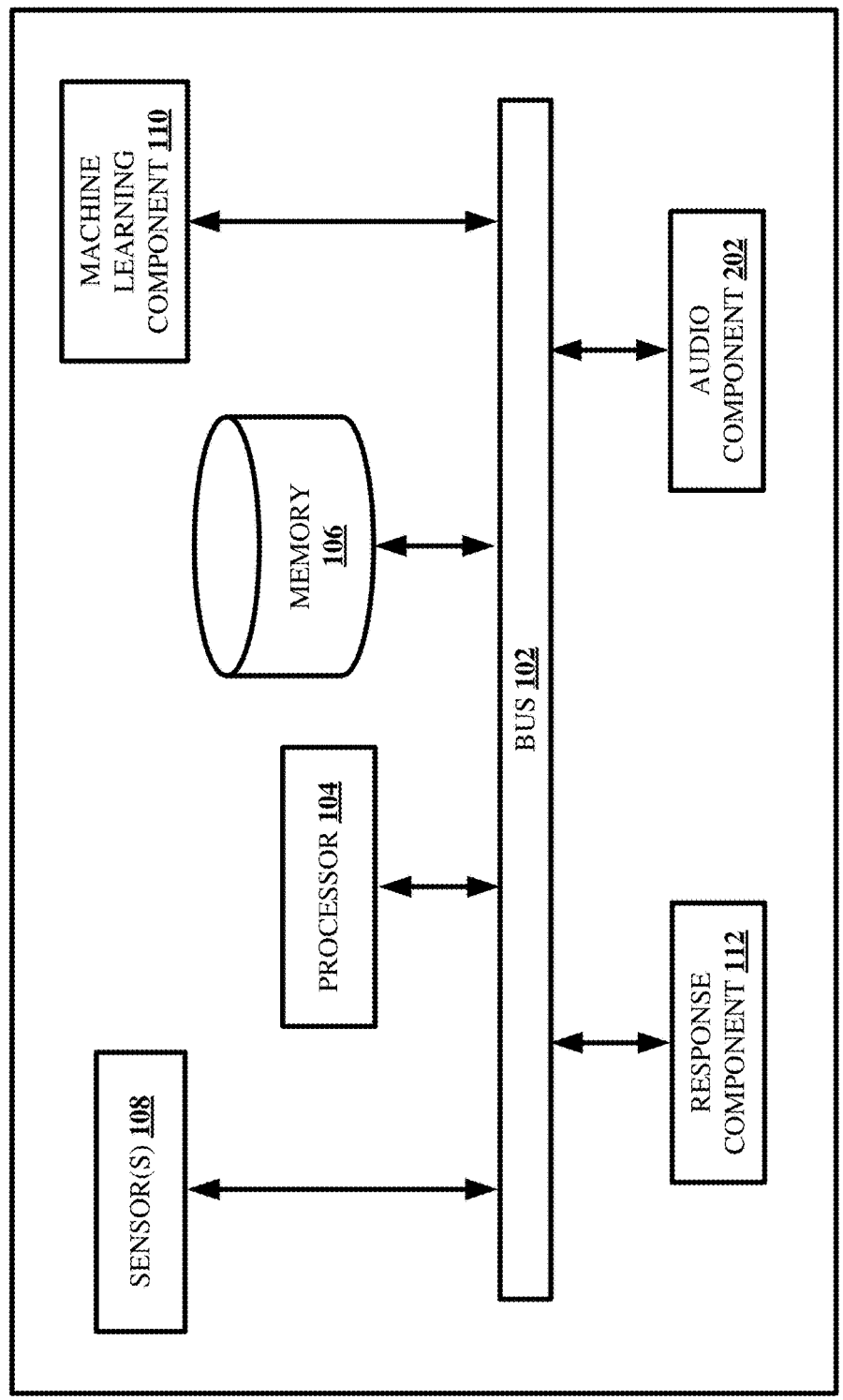
FIG. 2 illustrates a block diagram of an example, non-limiting system facilitating real-time response to defined symptoms including an audio component in accordance with one or more embodiments described herein.

FIG. 2 illustrates a block diagram of an example, non-limiting system 100 facilitating real-time response to defined symptoms including an audio component 202 in accordance with one or more embodiments described herein. Repetitive description of like elements employed in other embodiments described herein is omitted for sake of brevity. The audio component 202 can output audio responses. The audio responses can be, but not limited to, breathing exercise, sound of relaxing music, heartbeat sounds or other soothing sounds. The audio component 202 can output audio responses upon receiving signals from the response component 112 to output audio responses. It is appreciated that the response component 112 can transmit one or more signals to the audio component 202 to output one or more audio responses at a given moment. For example, the response component 112 can transmit signals to the audio component 202 to play breathing exercises while playing relaxing music softly in the background.

The type of audio response (e.g., different types of breathing exercises, different types of relaxing music, different types of heartbeat sounds, different types of soothing sounds, etc.) the audio component 202 deploys can be based on feedback analyzed by the machine learning component 110. For example, the machine learning component 110 can continually analyze sensor data from the sensors 108 to determine the defined symptoms of a user. Based on analyses by the machine learning component 110 whether a user's defined symptoms have improved (e.g., decreased) or increased, the response component 112 can change the type of audio response by transmitting one or more signals to the audio component 202 to deploy one or more different types of audio responses.

Figure 3:
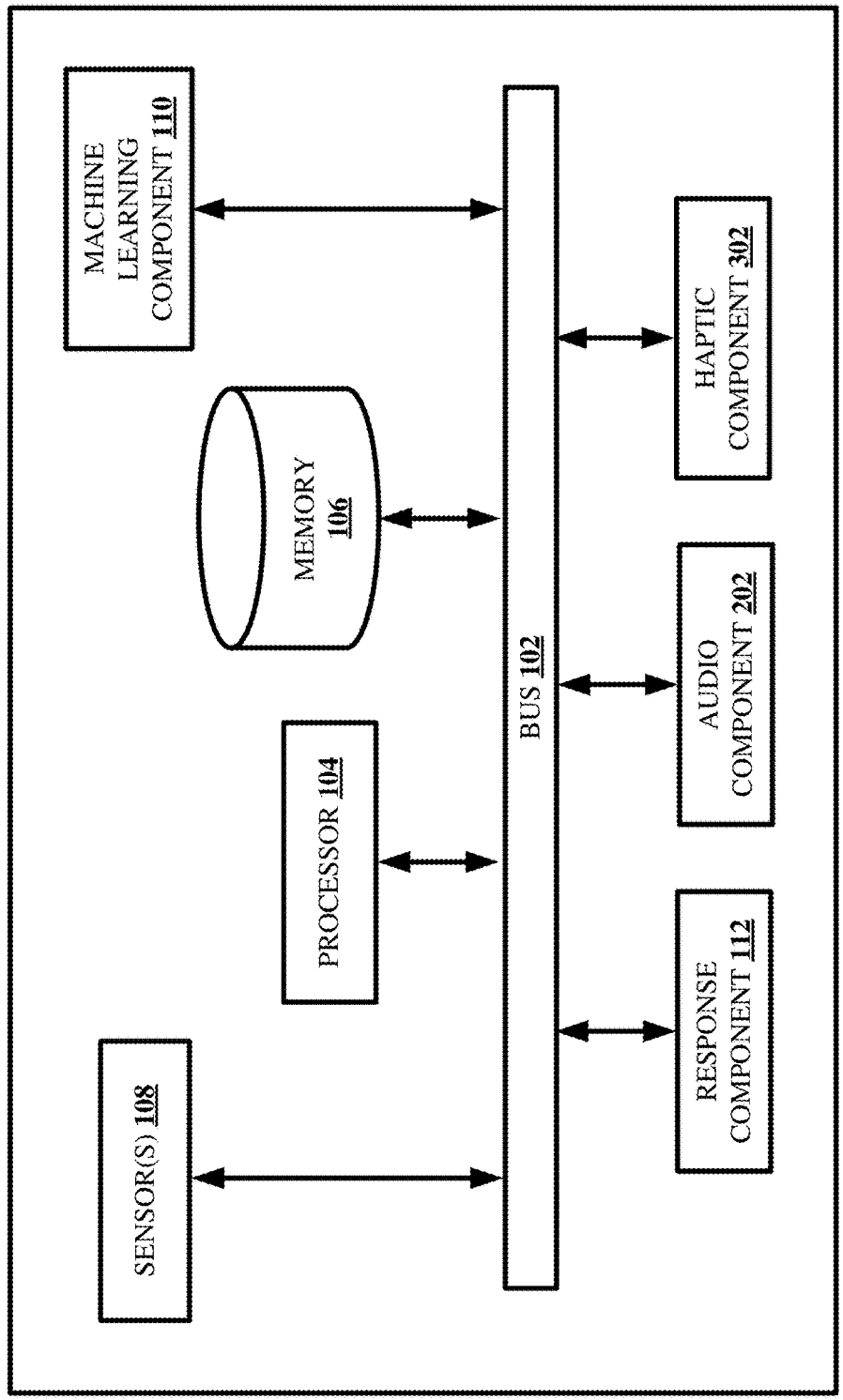
FIG. 3 illustrates a block diagram of an example, non-limiting system facilitating real-time response to defined symptoms including a haptic component in accordance with one or more embodiments described herein.

FIG. 3 illustrates a block diagram of an example, non-limiting system 100 facilitating real-time calming of stress or panic including a haptic component 302 in accordance with one or more embodiments described herein. Repetitive description of like elements employed in other embodiments described herein is omitted for sake of brevity. The haptic component 302 can provide haptic responses (e.g., massages). The haptic responses can be, but not limited to, shoulder massages or back massages. The haptic component 302 can output haptic responses upon receiving signals from the response component 112 to output haptic responses. It is appreciated that the response component 112 can transmit one or more signals to the haptic component 302 to output one or more haptic responses at a given moment. For example, the response component 112 can transmit signals to the haptic component 302 to provide shoulder massages and back massage at the same time.

The type of haptic response (e.g., shoulder massages, back massages, etc.) the haptic component 302 deploys can be based on feedback analyzed by the machine learning component 110. For example, the machine learning component 110 can continually analyze sensor data from the sensors 108 to determine the defined symptoms of the user. Based on analyses by the machine learning component 110 whether a user's defined symptoms have improved (e.g., decreased) or increased, the response component 112 can change the type of haptic response by transmitting one or more signals to the haptic component 302 to deploy one or more different types of haptic responses.

Figure 4:
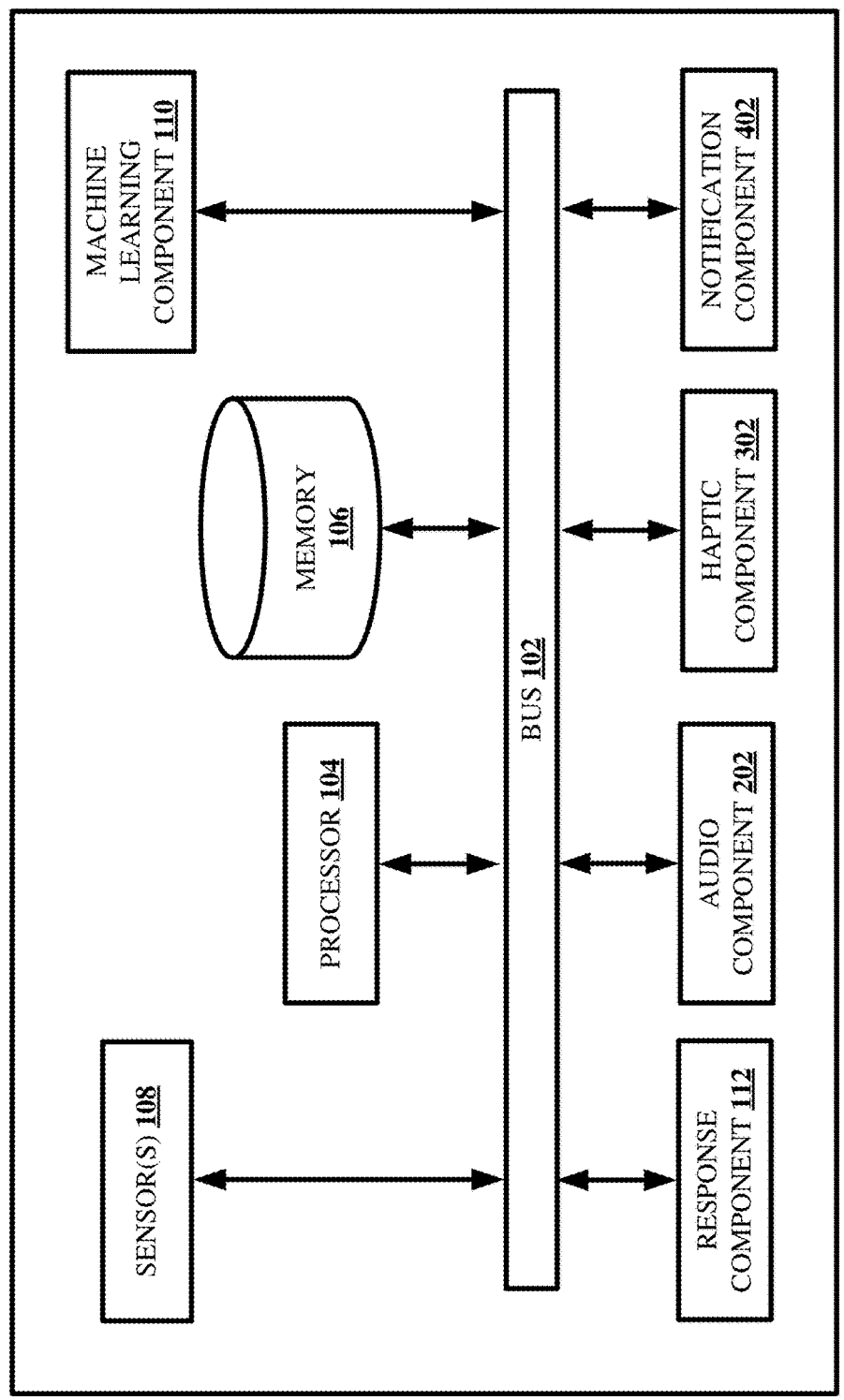
FIG. 4 illustrates a block diagram of an example, non-limiting system facilitating real-time response to defined symptoms including a notification component in accordance with one or more embodiments described herein.

FIG. 4 illustrates a block diagram of an example, non-limiting system 100 facilitating real-time response to defined symptoms including a notification component 402 in accordance with one or more embodiments described herein. Repetitive description of like elements employed in other embodiments described herein is omitted for sake of brevity. The notification component 402 can notify another person (e.g., a caregiver, a family member, a close friend, etc.) or emergency service if there is no detected improvement of the defined symptoms within a defined amount of time after detection of the defined symptoms. For example, the sensors 108 can continually monitor the audio of a room or area surrounding a user, detect a user's body vitals or monitor accelerometer data from movements exerted by a user. Based on these sensor data from the sensors 108, the machine learning component 110 can analyze and determine whether a user's defined symptoms have improved (e.g., decreased). If a determined amount of time has lapsed without signs of improvement, the notification component 402 can send an alert to designated persons to obtain help or notify emergency service for medical assistance. The notification component 402 can also send out alerts for help if a user's defined symptoms analyzed by the machine learning component 110 is higher than a determined threshold.

The notification component 402 can also notify designated persons (e.g., a caregiver, a family member, a close friend, etc.) or emergency service upon detection of a call for help from a user. Certain words can trigger the notification component 402 to alert help. For example, if the sensors 108 (e.g., a microphone) records a user screaming the word help, the machine learning component 110 can employ voice recognition to detect a call for help by the user, and the notification component 402 can alert help based on detection of a call for help by the user.

Figure 5:
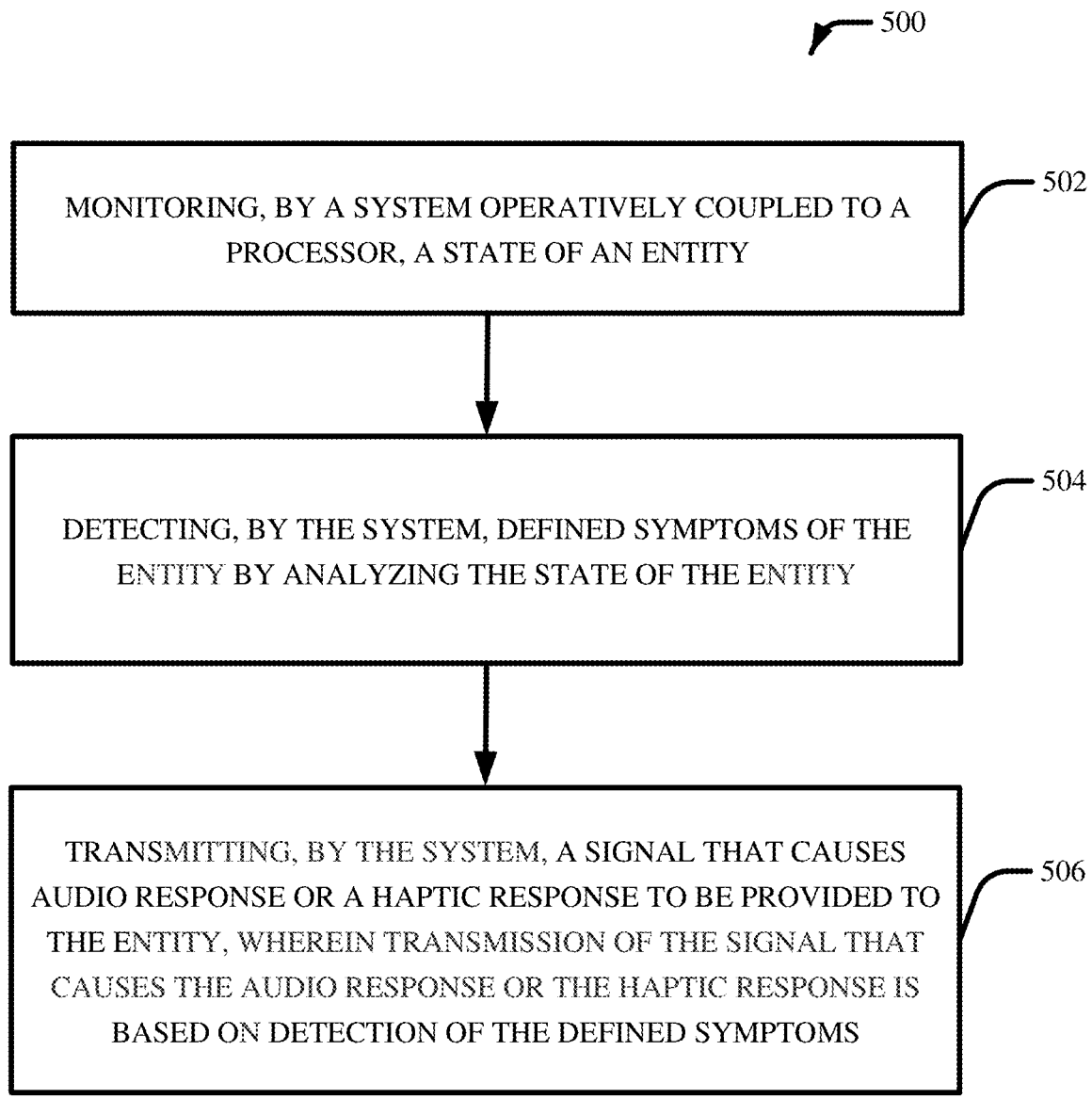
FIGS. 5-6 illustrate flow diagrams of example, non-limiting computer-implemented methods facilitating real-time response to defined symptoms in accordance with one or more embodiments described herein.

FIG. 5 illustrates a flow diagram of an example, non-limiting computer-implemented method 500 facilitating response to defined symptoms in accordance with one or more embodiments described herein. Repetitive description of like elements employed in other embodiments described herein is omitted for sake of brevity. At 502, the computer-implemented method 500 can comprise monitoring (e.g., via the one or more sensors), by the system 100 operatively coupled to the processor 104, a state of an entity. At 504, the computer-implemented method 500 can comprise detecting (e.g., via the machine learning component 110), by the system 100, defined symptoms of the entity by analyzing the state of the entity. At 506, the computer-implemented method 500 can comprise transmitting (e.g., via the response component 112), by the system 100, a signal that causes audio response or a haptic response to be provided to the entity, wherein transmission of the signal that causes the audio response or the haptic response is based on detection of the defined symptoms.

Figure 6:
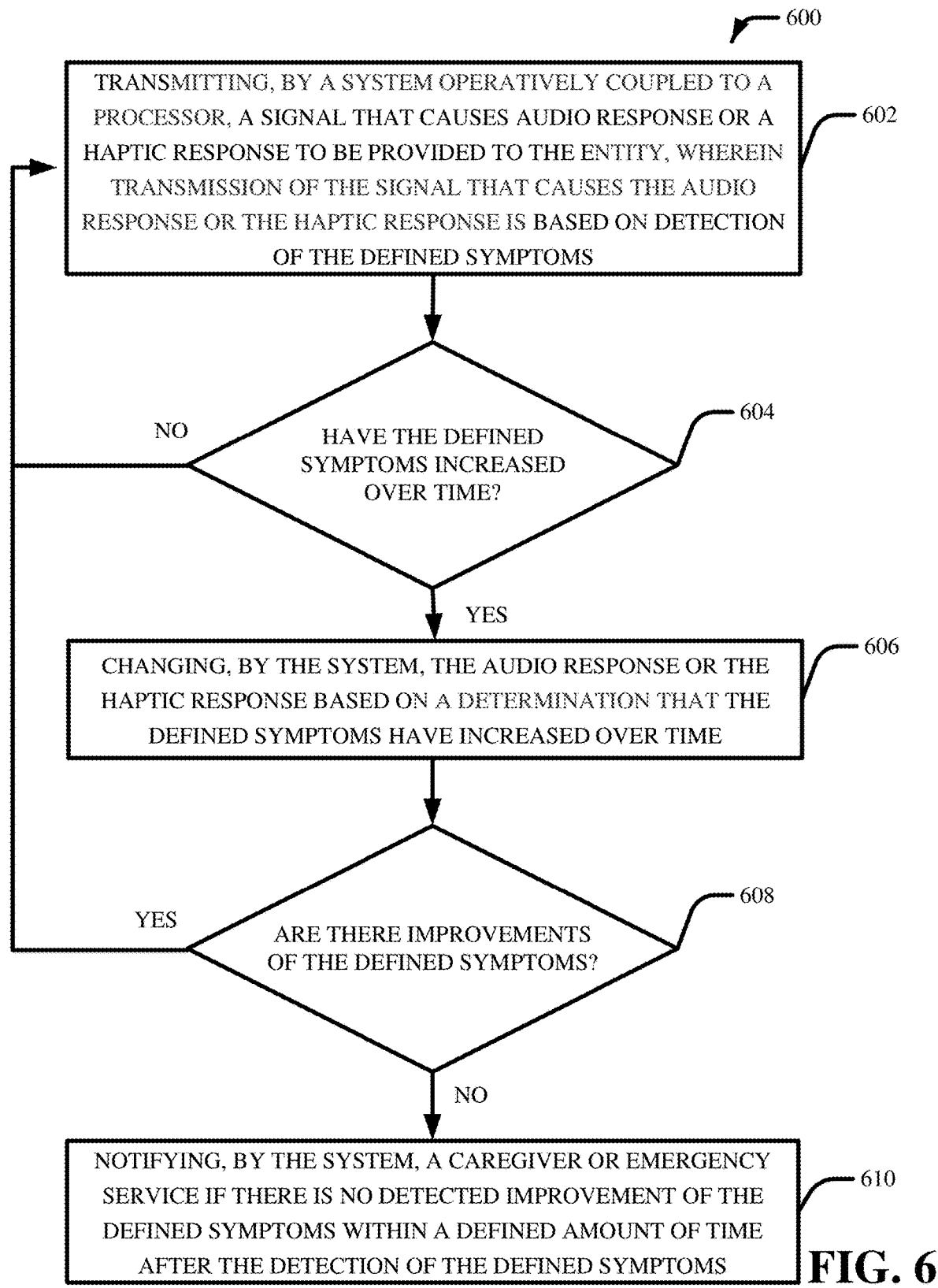

FIG. 6 illustrates a flow diagram of an example, non-limiting computer-implemented method 600 facilitating real-time response to defined symptoms in accordance with one or more embodiments described herein. Repetitive description of like elements employed in other embodiments described herein is omitted for sake of brevity. At 602, the computer-implemented method 600 can comprise transmitting (e.g., via the response component 112), by the system 100 operatively coupled to the processor 104, a signal that causes audio response or a haptic response to be provided to the entity, wherein transmission of the signal that causes the audio response or the haptic response is based on detection of the defined symptoms. At 604, the computer-implemented method 600 can comprise determining (e.g., via the response component 112), by the system 100, whether the defined symptoms have increased over time. If no, the process can continue at 602. If yes, the process can proceed to 606. At 606, the computer-implemented method 600 can comprise changing (e.g., via the response component 112), by the system 100, the audio response or the haptic response based on a determination that the defined symptoms have increased over time. At 608, the computer-implemented method 600 can comprise determining (e.g., via the notification component 402), by the system 100, whether there are improvements of the defined symptoms. If yes, the process can continue at 602. If no, the process can proceed to 610. At 610, the computer-implemented method 600 can comprise notifying (e.g., via the notification component 402), by the system 100, a caregiver or emergency service if there is no detected improvement of the defined symptoms within a defined amount of time after the detection of the defined symptoms.

Figure 7:
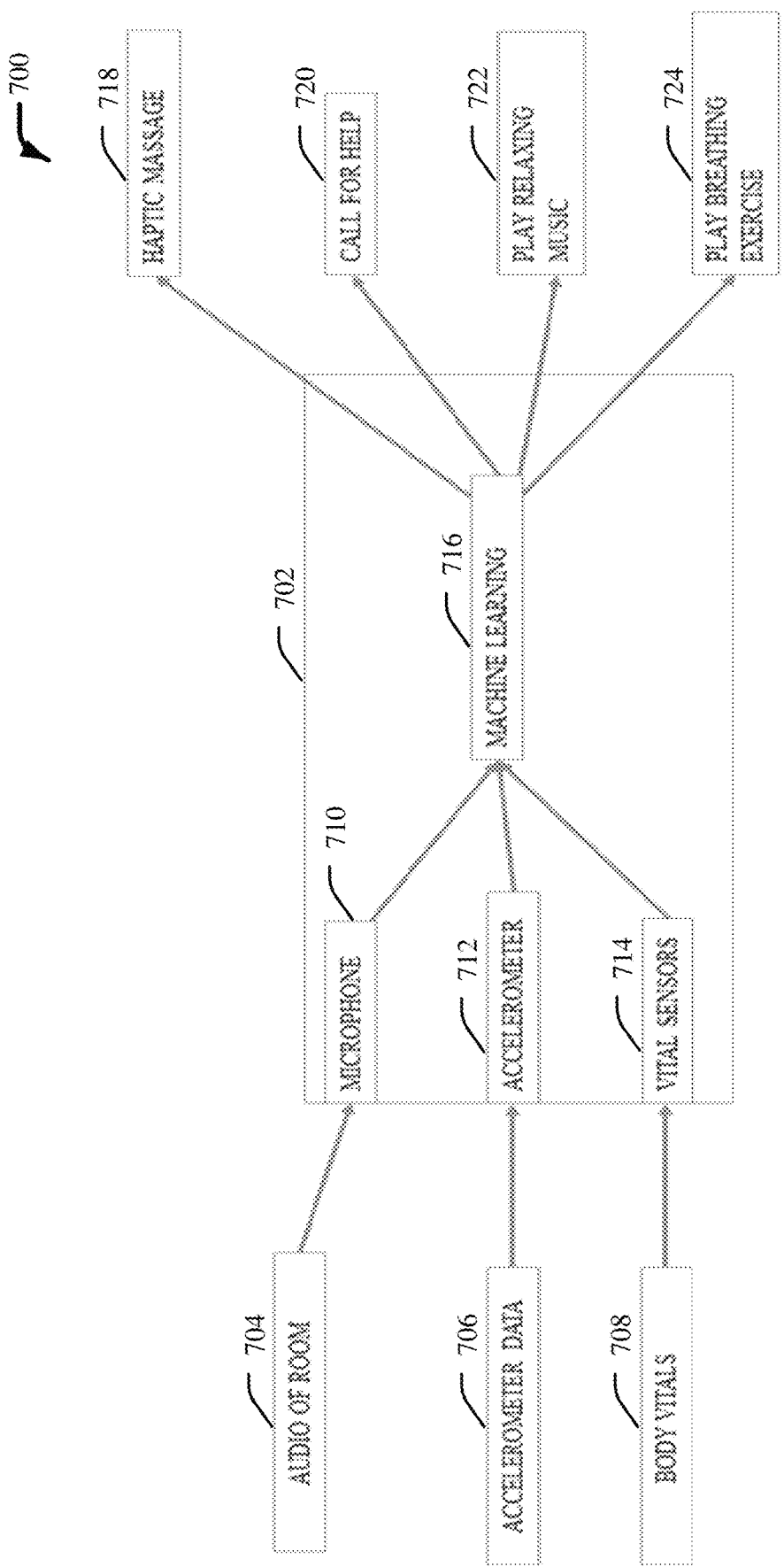
FIG. 7 illustrates a block diagram of an example, non-limiting system facilitating real-time response to defined symptoms in accordance with one or more embodiments described herein.

FIG. 7 illustrates a block diagram of an example, non-limiting system 700 facilitating real-time response to defined symptoms in accordance with one or more embodiments described herein. Repetitive description of like elements employed in other embodiments described herein is omitted for sake of brevity. The system 700 can comprise IoT device 702. The IoT device 702 can comprise a microphone 710, an accelerometer 712 and vital sensors 714. The microphone 710 can monitor audio of room 704. The accelerometer 712 can detect accelerometer data 706. The vital sensors 714 can monitor body vitals 708. The device 702 can employ machine learning 716 (e.g., analytics, voice recognition, machine learning, etc.) to analyze audio of room 704, accelerometer data 706 and body vitals 708 for detection of the defined symptoms. The audio of room 704 can include words or vocalization by a user indicating signs of the defined symptoms or a call for help. The accelerometer data 706 can include body movements such as jerky movements. Body vitals 708 can include, but not limited to, body temperature, blood pressure, pulse or heart rate, and breathing rate or respiratory rate. If the defined symptoms are detected, the device 702 can cause a number of responses such as a call for help 720 or soothing responses including haptic massage 718, play relaxing music 722 or play breathing exercise 724.

Figure 8:
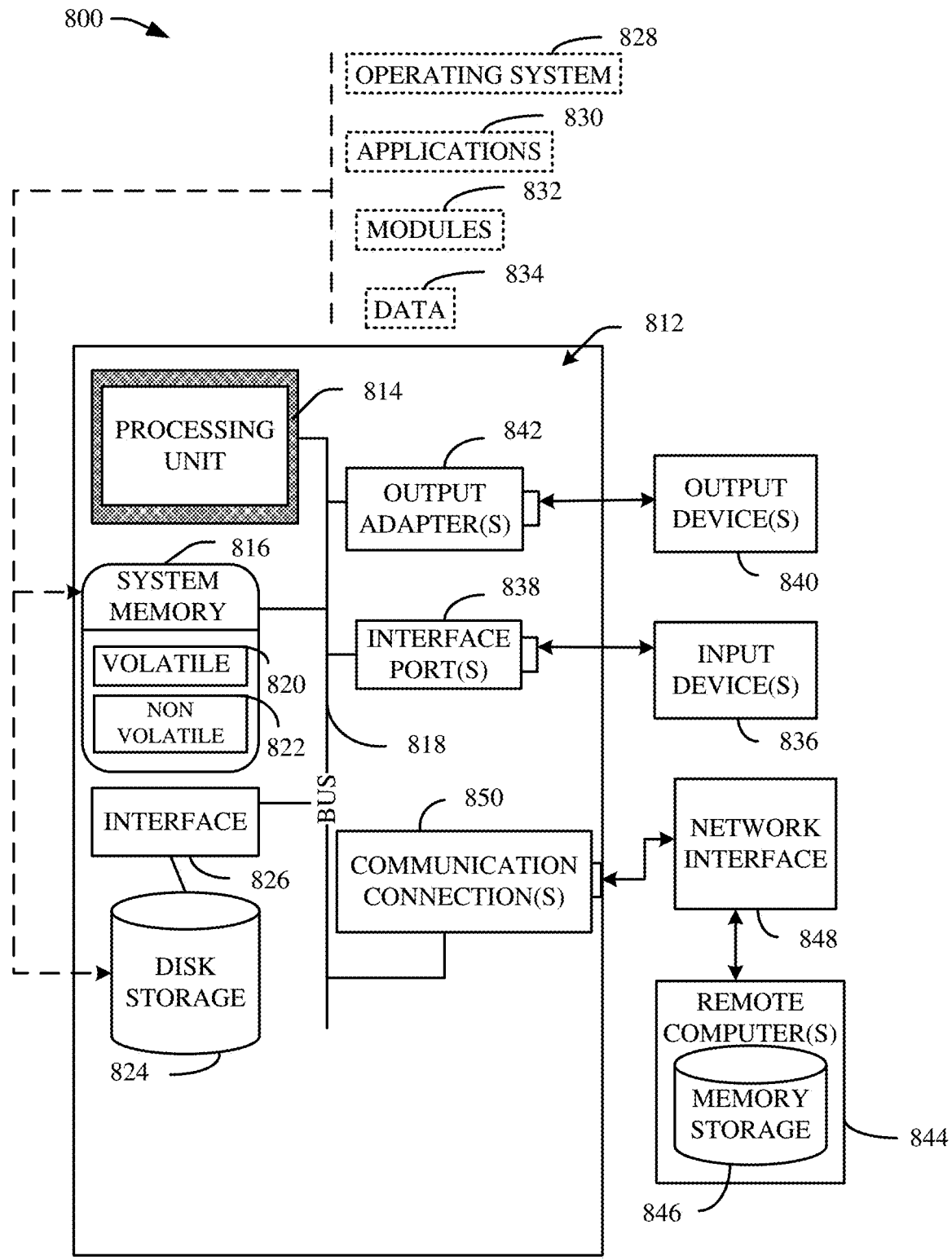
FIG. 8 illustrates a block diagram of an example, non-limiting operating environment in which one or more embodiments described herein can be facilitated.

In order to provide a context for the various aspects of the disclosed subject matter, FIG. 8 as well as the following discussion are intended to provide a general description of a suitable environment in which the various aspects of the disclosed subject matter can be implemented. FIG. 8 illustrates a block diagram of an example, non-limiting operating environment in which one or more embodiments described herein can be facilitated. Repetitive description of like elements employed in other embodiments described herein is omitted for sake of brevity.

With reference to FIG. 8, a suitable operating environment 800 for implementing various aspects of this disclosure can also include a computer 812. The computer 812 can also include a processing unit 814, a system memory 816, and a system bus 818. The system bus 818 couples system components including, but not limited to, the system memory 816 to the processing unit 814. The processing unit 814 can be any of various available processors. Dual microprocessors and other multiprocessor architectures also can be employed as the processing unit 814. The system bus 818 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 816 can also include volatile memory 820 and nonvolatile memory 822. The basic input/output system (BIOS), containing the basic routines to transfer information between elements within the computer 812, such as during start-up, is stored in nonvolatile memory 822. Computer 812 can also include removable/non-removable, volatile/non-volatile computer storage media. FIG. 8 illustrates, for example, a disk storage 824. Disk storage 824 can also include, but is not limited to, devices like a magnetic disk drive, floppy disk drive, tape drive, Jaz drive, Zip drive, LS-100 drive, flash memory card, or memory stick. The disk storage 824 also can include storage media separately or in combination with other storage media. To facilitate connection of the disk storage 824 to the system bus 818, a removable or non-removable interface is typically used, such as interface 826. FIG. 8 also depicts software that acts as an intermediary between users and the basic computer resources described in the suitable operating environment 800. Such software can also include, for example, an operating system 828. Operating system 828, which can be stored on disk storage 824, acts to control and allocate resources of the computer 812.

System applications 830 take advantage of the management of resources by operating system 828 through program modules 832 and program data 834, e.g., stored either in system memory 816 or on disk storage 824. It is to be appreciated that this disclosure can be implemented with various operating systems or combinations of operating systems. A user enters commands or information into the computer 812 through input device(s) 836. Input devices 836 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 814 through the system bus 818 via interface port(s) 838. Interface port(s) 838 include, for example, a serial port, a parallel port, a game port, and a universal serial bus (USB). Output device(s) 840 use some of the same type of ports as input device(s) 836. Thus, for example, a USB port can be used to provide input to computer 812, and to output information from computer 812 to an output device 840. Output adapter 842 is provided to illustrate that there are some output devices 840 like monitors, speakers, and printers, among other output devices 840, which require special adapters. The output adapters 842 include, by way of illustration and not limitation, video and sound cards that provide a means of connection between the output device 840 and the system bus 818. It should be noted that other devices and/or systems of devices provide both input and output capabilities such as remote computer(s) 844.

Computer 812 can operate in a networked environment using logical connections to one or more remote computers, such as remote computer(s) 844. The remote computer(s) 844 can be a computer, a server, a router, a network PC, a workstation, a microprocessor based appliance, a peer device or other common network node and the like, and typically can also include many or all of the elements described relative to computer 812. For purposes of brevity, only a memory storage device 846 is illustrated with remote computer(s) 844. Remote computer(s) 844 is logically connected to computer 812 through a network interface 848 and then physically connected via communication connection 850. Network interface 848 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 850 refers to the hardware/software employed to connect the network interface 848 to the system bus 818. While communication connection 850 is shown for illustrative clarity inside computer 812, it can also be external to computer 812. The hardware/software for connection to the network interface 848 can also include, for exemplary purposes only, internal and external technologies such as, modems including regular telephone grade modems, cable modems and DSL modems, ISDN adapters, and Ethernet cards.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 9:
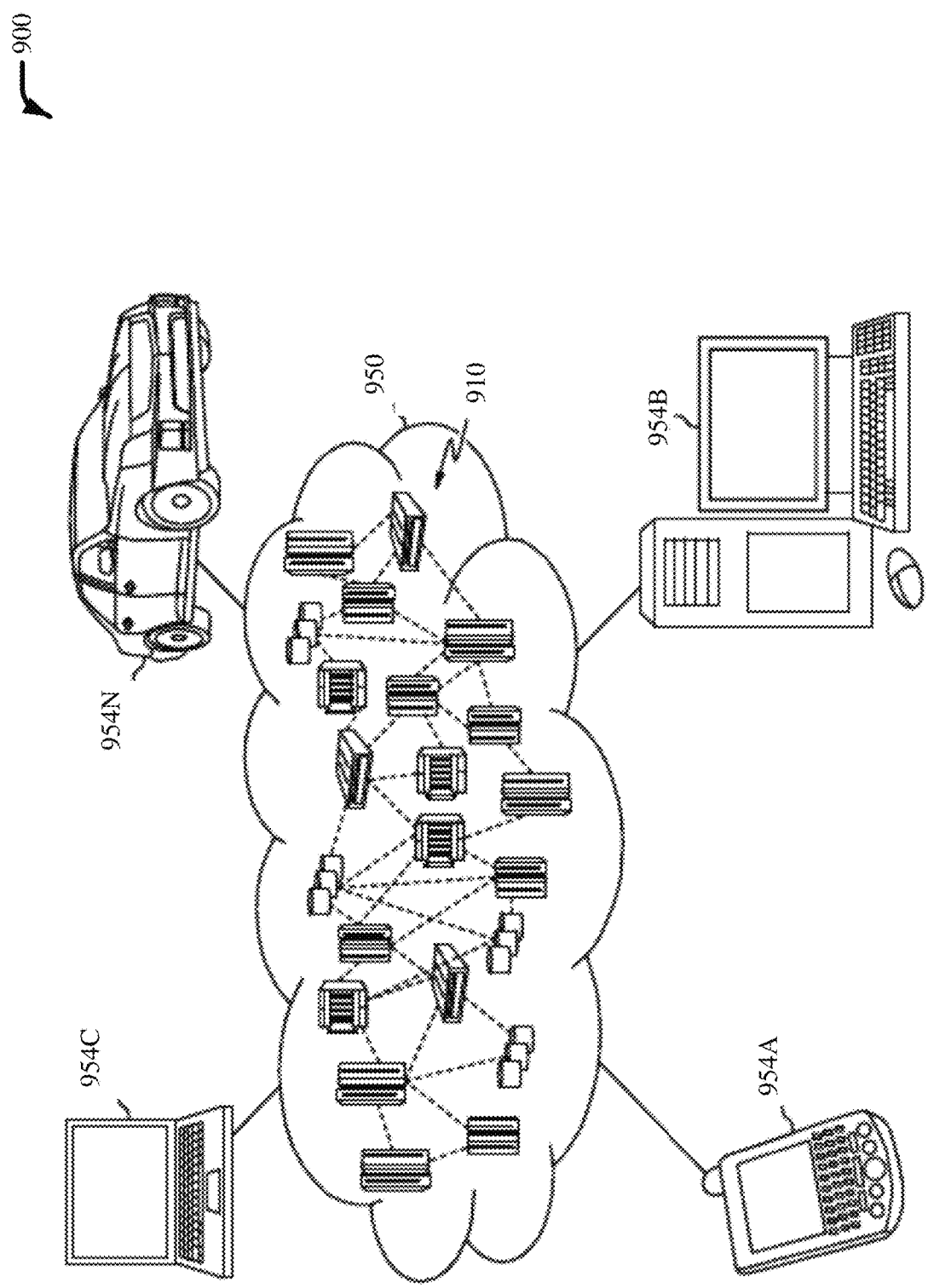
FIG. 9 illustrates a block diagram of an example, non-limiting cloud computing environment in accordance with one or more embodiments described herein.

Referring now to FIG. 9, an illustrative cloud computing environment 950 is depicted. As shown, cloud computing environment 950 includes one or more cloud computing nodes 910 with which local computing devices used by cloud consumers, such as, for example, personal digital assistant (PDA) or cellular telephone 954A, desktop computer 954B, laptop computer 954C, and/or automobile computer system 954N may communicate. Nodes 910 may communicate with one another. They may be grouped (not shown) physically or virtually, in one or more networks, such as Private, Community, Public, or Hybrid clouds as described hereinabove, or a combination thereof. This allows cloud computing environment 950 to offer infrastructure, platforms and/or software as services for which a cloud consumer does not need to maintain resources on a local computing device. It is understood that the types of computing devices 954A-N shown in FIG. 9 are intended to be illustrative only and that computing nodes 910 and cloud computing environment 950 can communicate with any type of computerized device over any type of network and/or network addressable connection (e.g., using a web browser).

Figure 10:
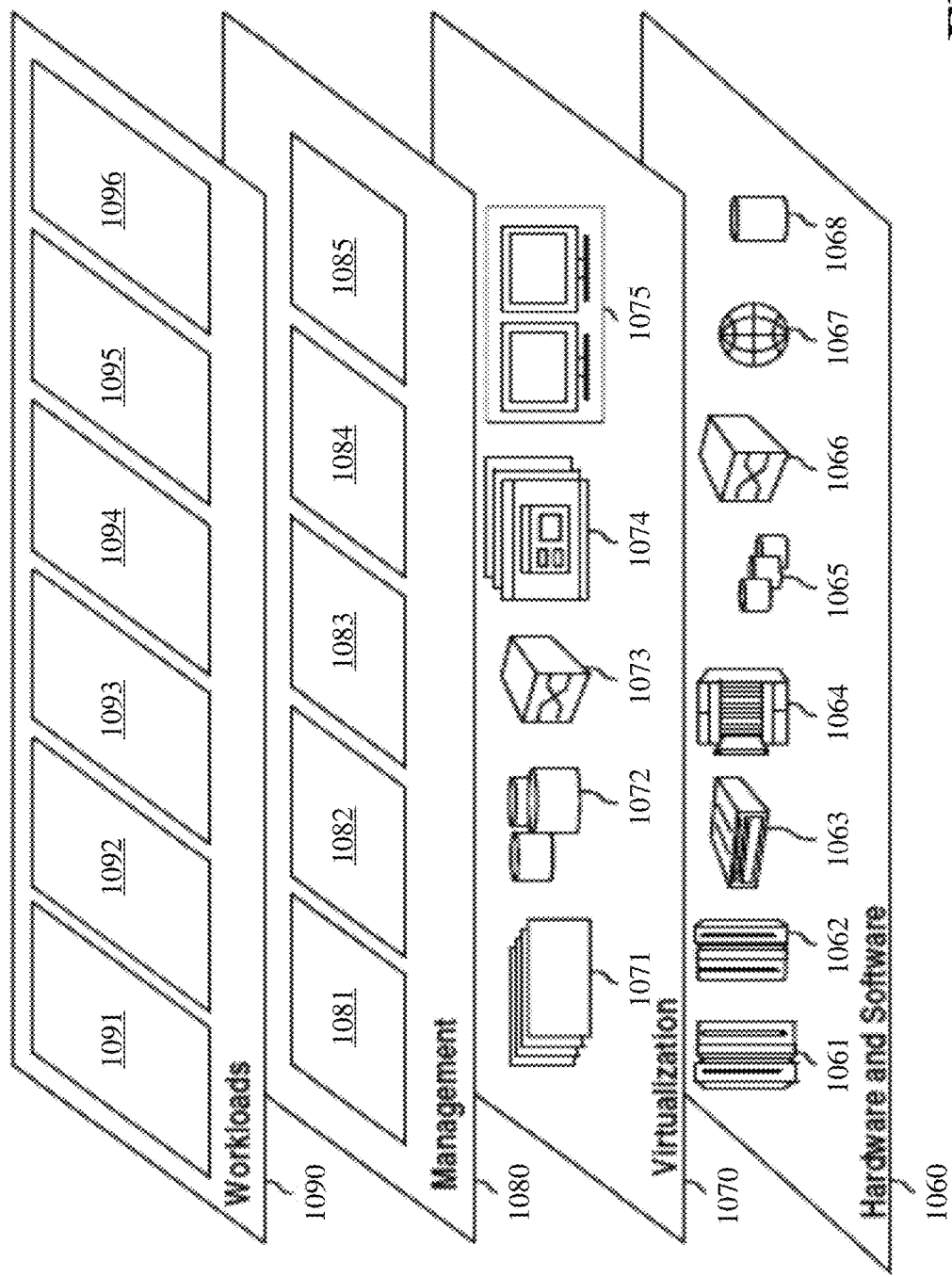
FIG. 10 illustrates a block diagram of example, non-limiting abstraction model layers in accordance with one or more embodiments described herein.

Referring now to FIG. 10, a set of functional abstraction layers provided by cloud computing environment 950 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 1060 includes hardware and software components. Examples of hardware components include: mainframes 1061; RISC (Reduced Instruction Set Computer) architecture based servers 1062; servers 1063; blade servers 1064; storage devices 1065; and networks and networking components 1066. In some embodiments, software components include network application server software 1067 and database software 1068.

Virtualization layer 1070 provides an abstraction layer from which the following examples of virtual entities may be provided: virtual servers 1071; virtual storage 1072; virtual networks 1073, including virtual private networks; virtual applications and operating systems 1074; and virtual clients 1075.

In one example, management layer 1080 may provide the functions described below. Resource provisioning 1081 provides dynamic procurement of computing resources and other resources that are utilized to perform tasks within the cloud computing environment. Metering and Pricing 1082 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1083 provides access to the cloud computing environment for consumers and system administrators. Service level management 1084 provides cloud computing resource allocation and management such that required service levels are met. Service Level Agreement (SLA) planning and fulfillment 1085 provide pre-arrangement for, and procurement of, cloud computing resources for which a future requirement is anticipated in accordance with an SLA.

Workloads layer 1090 provides examples of functionality for which the cloud computing environment may be utilized. Non-limiting examples of workloads and functions which may be provided from this layer include: mapping and navigation 1091; software development and lifecycle management 1092; virtual classroom education delivery 1093; data analytics processing 1094; transaction processing 1095; and mobile desktop 1096.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability;

multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components;
   a processor, operably coupled to the memory, and that executes the computer executable components stored in the memory, wherein the computer executable components comprise:
   a machine learning component configured to:
      determines, via an altimeter, that an entity known to have a fear of heights is undergoing an increase in altitude,
      based on the determination of the increase in altitude, monitors, via one or more sensors, a state of the entity, and
      detects, by analyzing the state of the entity, that a defined bodily symptom of the entity is increasing; and
   a response component that:
      transmits a first signal that causes an audio device to produce an audio response selected to decrease the defined bodily symptom, and
      in response to a determination that the defined bodily symptom has not decreased as a result of the audio response, transmits a second signal that causes a device to produce a haptic response to the entity, wherein the haptic response is selected to decrease the defined bodily symptom.

2. The system of claim 1, wherein the audio response is a breathing exercise, music or heartbeat sound.

3. The system of claim 1, wherein the haptic response is a shoulder massage or back massage.

4. The system of claim 1, wherein the audio response or the haptic response are generated at a time period less than 1 minute from time of the detection of the defined bodily symptom.

5. The system of claim 1, wherein the response component changes the audio response or the haptic response based on a determination that the defined bodily symptom has increased over time.

6. The system of claim 1, wherein the one or more sensors further comprise at least one of a microphone to detect voice of the entity, a heart rate monitor to detect heart rate of the entity, a pulse monitor to detect pulse of the entity, an accelerometer to measure body movement of the entity, a thermometer to measure body temperature of the entity, a galvanic skin response (GSR) sensor to measure electrodermal activity of the entity, a pedometer to count steps of the entity, a sleep monitor to track sleep pattern of the entity, a global positioning system (GPS) to track geolocation of the entity, an electromyography (EMG) sensor to detect muscle tension of the entity, a barometer to measure atmospheric pressure surrounding the entity, a light sensor to measure light intake by the entity, a respiratory rate monitor to measure breathing rate of the entity, a blood pressure monitor to measure blood pressure of the entity, an electrocardiographic (ECG) sensor to monitor electrical activity of a heart of the entity, or a pulse oximeter to monitor blood oxygen level of the entity.

7. The system of claim 1, wherein the machine learning component is further configured to utilize voice recognition to detect a call for help from the entity.

8. The system of claim 7, further comprising a notification component configured to notify a caregiver or an emergency service upon detection of the call for help from the entity.

9. The system of claim 1, further comprising a notification component configured to notify a caregiver or emergency service if the defined bodily symptom meets a threshold level.

10. A computer-implemented method, comprising:
determining, by a system operatively coupled to a processor, via an altimeter, that an entity known to have a fear of heights is undergoing an increase in altitude;
in response to the determination of the increase in altitude:
   monitoring, by the system operatively coupled to a processor, via one or more sensors, a state of the entity;
   detecting, by the system, by analyzing the state of the entity, that a defined bodily symptom of the entity is increasing;
   transmitting, by the system, a first signal that causes an audio device to produce an audio response selected to decrease the defined bodily symptom; and
   in response to determining that the defined bodily symptom has not decreased as a result of the audio response, transmitting, by the system, a second signal that causes a device to produce a haptic response to the entity, wherein the haptic response is selected to decrease the defined bodily symptom.

11. The computer-implemented method of claim 10, wherein the audio response is a breathing exercise, music or heartbeat sound.

12. The computer-implemented method of claim 10, wherein the haptic response is a shoulder massage or back massage.

13. The computer-implemented method of claim 10, further comprising changing, by the system, the audio response or the haptic response based on a determination that the defined bodily symptom has increased over time.

14. The computer-implemented method of claim 10, further comprising utilizing, by the system, voice recognition to detect a call for help from the entity.

15. The computer-implemented method of claim 14, further comprising notifying, by the system, a caregiver or an emergency service upon detection of the call for help from the entity.

16. The computer-implemented method of claim 10, further comprising notifying, by the system, a caregiver or emergency service if the defined bodily symptom meets a threshold level.

17. A computer program product comprising a non-transitory computer readable medium having program instructions embodied therewith, the program instructions executable by a processor to cause the processor to:
determine, via an altimeter, that an entity known to have a fear of heights is undergoing an increase in altitude;
in response to the determination of the increase in altitude:
   monitor, via one or more sensors, a state of the entity;
   detect, by analyzing the state of the entity, that a defined bodily symptom of the entity is increasing; and
   transmit a first signal that causes an audio device to produce an audio response selected to decrease the defined bodily symptom; and
   in response to determining that the defined symptom has not decreased as a result of the audio response, transmitting a second signal that causes a device to produce a haptic response to the entity, wherein the haptic response is selected to decrease the defined bodily symptom.

18. The computer program product of claim 17, wherein wherein the audio response is a breathing exercise, music or heartbeat sound.

19. The computer program product of claim 17, wherein the wherein the haptic response is a shoulder massage or back massage.

20. The computer program product of claim 17, wherein the program instructions are further executable to cause the processor to:
notify a caregiver or emergency service if the defined bodily symptom meets a threshold level.

* * * * *